United States Patent [19]

Verheyden et al.

[11] Patent Number: 4,612,314

[45] Date of Patent: Sep. 16, 1986

[54] SUBSTITUTED 9-(1 OR 3-MONOACYLOXY OR 1,3-DIACYLOXY-2-PROPOXYMETHYL) PURINES AS ANTIVIRAL AGENT

[75] Inventors: Julien P. H. Verheyden, Los Altos; John C. Martin, Redwood City, both of Calif.

[73] Assignee: Syntex (U.S.A.) Inc., Palo Alto, Calif.

[21] Appl. No.: 744,582

[22] Filed: Jun. 13, 1985

Related U.S. Application Data

[63] Continuation of Ser. No. 451,262, Dec. 22, 1982, which is a continuation-in-part of Ser. No. 344,703, Feb. 1, 1982, abandoned.

[51] Int. Cl.⁴ .................. C07D 473/18; A61K 31/52
[52] U.S. Cl. ............................ 514/261; 514/262; 544/276; 544/277
[58] Field of Search ............... 544/276, 277; 514/261, 514/262

[56] References Cited

U.S. PATENT DOCUMENTS 4,323,573 4/1982 Schaeffer ....................... 544/276

Primary Examiner—Nicholas S. Rizzo

Attorney, Agent, or Firm—Annette M. Moore; Tom M. Moran

[57] ABSTRACT

Compounds useful as antiviral agents are defined by the following formula:

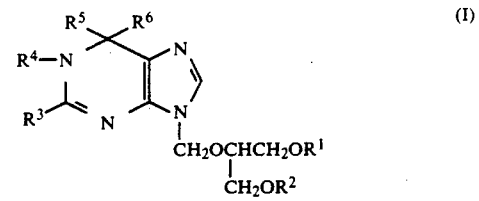

and the pharmaceutically acceptable acid addition salts thereof wherein $R^1$ and $R^2$ are both —C(O)$R^7$ wherein $R^7$ is 1-adamantyl;

$R^3$ is amino;

(a) $R^6$ is hydrogen or amino and $R^4$ together with $R^5$ is a bond; or (b) $R^5$ together with $R^6$ is a keto group and $R^4$ is hydrogen.

5 Claims, No Drawings

SUBSTITUTED 9-(1 OR 3-MONOACYLOXY OR 1,3-DIACYLOXY-2-PROPOXYMETHYL) PURINES AS ANTIVIRAL AGENT

BACKGROUND OF THE INVENTION

This is a continuation of U.S. Ser. No. 451,262 filed Dec. 22, 1982 which is a continuation-in-part, of U.S. Ser. No. 344,703 filed Feb. 1, 1982 now abandoned.

1. Field of the Invention

This invention relates to substituted 9-(1 or 3-monoacyloxy or 1,3-diacyloxy-2-propoxymethyl)purines and pharmaceutically acceptable acid addition salts thereof which are useful as antiviral agents. The invention also relates to a pharmaceutical composition containing the above compounds in combination with a suitable non-toxic carrier, the composition being useful in combatting viral infections. The invention also relates to a process for preparing the compounds of the invention.

2. Related Disclosure

Viral infections are widespread and result in a wide variety of symptoms. Some viral infections are easily overcome by the body's defense mechanism, but when this defense mechanism is impaired these infections can lead to permanent damage, e.g., blindness, and even to death. One such family of viruses which may cause serious infections is the herpes virus group.

The drugs presently used to treat viral infections are ineffective in many cases or, if effective, are needed in large and/or continuous dosages which produce serious side-effects and/or toxicity. Therefore there is a need for an effective antiviral agent which is effective at lower dosages than the presently available drugs, thus diminishing the chance of possible side-effects and toxicity.

U.S. Pat. No. 4,199,574 discloses compounds represented by the following generic formula:

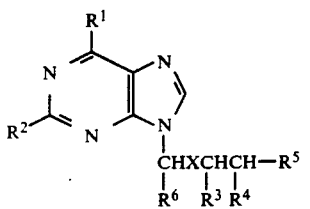

wherein X is sulphur or oxygen, $R^1$ is hydrogen, halogen, hydroxy, alkoxy, azide, thio, alkylthio, amino, alkylamino or dialkylamino; $R^2$ is hydrogen, halogen, alkylthio, acylamino, amino or azide; $R^3$ is hydrogen, straight or branch chain or cyclic alkyl, hydroxyalkyl, benzyloxyalkyl or phenyl; $R^4$ is hydrogen, hydroxy or alkyl; $R^5$ is hydrogen, hydroxy, amino, alkyl, hydroxyalkyl, benzyloxy, benzoyloxy, benzoyloxymethyl, sulphamoyloxy, phosphate, carboxypropiamyloxy, straight chain or cyclic acyloxy having from 1 to 8 carbon atoms e.g., acetoxy or substituted carbamoyl group of formula NHCO-Z wherein Z is alkyl, aryl or aralkyl optionally substituted by one or more of sulphonyl, amino, carbamoyl or halogen; $R^6$ is hydrogen or alkyl, provided that when X is oxygen and $R^2R^3$, $R^4$, and $R^6$ are hydrogen, $R^1$ is not amino or methylamino when $R^5$ is hydrogen or hydroxy, or a salt thereof.

The class of compounds represented by the above formula and the pharmaceutically acceptable acid addition salts thereof are described to exhibit antiviral activity. See also Tetrahedron Letters, 21, 327-30 (1980), U.S. Pat. No. 4,294,831 and U.S. Pat. No. 4,347,360.

SUMMARY OF THE INVENTION

It has now been discovered that substituted 9-(1 or 3-monoacyloxy- or 1,3-diacyloxy-2-propoxymethyl)purines and the salts thereof are particularly active antiviral agents.

The first aspect of the present invention is the compound of the following formula:

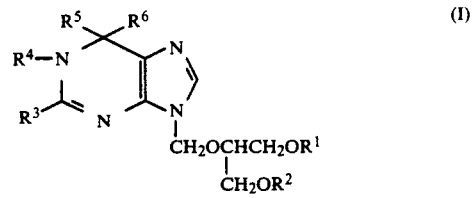

and the pharmaceutically acceptable acid addition salts thereof wherein $R^1$ is hydrogen or $-C(O)R^7$ wherein $R^7$ is hydrogen, alkyl of one to nineteen carbon atoms, hydroxyalkyl of one to eight carbon atoms, alkoxyalkyl of two to nine carbon atoms, alkenyl of two to nineteen carbon atoms, phenyl, 1-adamantyl or 2-carboxyethyl and the pharmaceutically acceptable alkali metal salts thereof;

$R^2$ is $-C(O)R^7$ wherein $R^7$ is as defined above;

$R^3$ is hydrogen, halo, thio, lower alkylthio of one to six carbon atoms, azido, $NR^9R^{10}$ wherein $R^9$ and $R^{10}$ are independently hydrogen or lower alkyl of one to six carbon atoms or -NHC(O)$R^8$ wherein $R^8$ is hydrogen, alkyl of one to nineteen carbon atoms or 1-adamantyl; and (a) $R^6$ is hydrogen, halo, lower alkoxy of one to six carbon atoms, azido, thio, lower alkylthio of one to six carbon atoms, -$NR^9R^{10}$ wherein $R^9$ and $R^{10}$ are as defined above or -NHC(O)$R^8$ wherein $R^8$ is as defined above and $R^4$ together with $R^5$ is a bond; or (b) $R^5$ together with $R^6$ is a keto group and $R^4$ is hydrogen.

Another aspect of the invention relates to pharmaceutical compositions for antiviral use comprising the compounds of the instant invention and a suitable carrier.

A further aspect of the invention is a method of treating viral infections consisting of administering a compound of the present invention or a composition containing same.

Another aspect of the invention are the novel compounds of formulas (IXa) and (XIV)(infra) wherein A is hydrogen which are useful as intermediates and as antiviral agents.

Yet another aspect of the invention is a process for preparing the compounds of formula (I) which comprises esterifying a compound of formula (X) or (XIV) infra.

DETAILED DESCRIPTION AND PREFERRED EMBODIMENT

As used in the specification and appended claims, unless specified to the contrary, the following terms have the meaning indicated.

The term "alkyl" refers to a straight or branched chain monovalent substituent consisting solely of carbon and hydrogen, containing no unsaturation and having one to nineteen carbon atoms. Examples of alkyl are methyl, n-butyl, 2-methyl-2-propyl, n-octyl, n-decyl, n-tetradecyl and n-nonadecyl. The term "lower alkyl" refers to alkyl groups as defined above but containing one to six carbon atoms. The term "alkenyl" refers to a straight or branched chain monovalent substituent consisting solely of carbon and hydrogen, containing one or more double bonds and having two to nineteen carbon atoms. Examples of "alkenyl" are propenyl, pentenyl, heptenyl, dodecenyl, dodecadienyl, pentadecenyl and pentadecadienyl. The term "1-adamantyl" refers to the following ring structure.

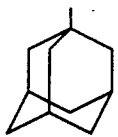

"Lower alkoxy" refers to "lower alkyl-O-" wherein "lower alkyl" is as defined above. Examples of "lower alkoxy" are methoxy, ethoxy, i-butoxy and n-hexyloxy. The term "alkoxyalkyl" refers to alkyl-O-alkylene wherein alkyl is as defined above and alkylene is a divalent alkyl group. Examples of "alkoxyalkyl" are methoxymethyl, i-propoxymethyl, n-octanyloxymethyl and ethoxypropyl. The term "lower alkylthio" refers to "lower alkyl-S-" wherein "lower alkyl" is as defined above. Examples of "lower alkylthio" are methylthio, n-propylthio and n-pentylthio. "Thio" refers to —SH. "Amino" refers to —NH$_2$. "Azido" refers to N$_3$. "Halo" refers to fluoro, chloro and bromo. "2-Carboxyethyl" refers to HOOCCH$_2$CH$_2$-.

"Pharmaceutically acceptable acid addition salts" refers to those salts which possess the biological effectiveness and properties of the free compound and which are not biologically or otherwise undesirable. Suitable acids for salt formation are inorganic acids such as hydrochloric acid, hydrobromic acid, sulfuric acid, phosphoric acid and the like, and organic acids such as trifluoroacetic acid, menthanesulfonic acid, ethanesulfonic acid, p-toluenesulfonic acid and the like.

"Pharmaceutically acceptable alkali metal salts" refers to the metal salts of the free carboxy group of the carboxyethyl group. Examples of alkali metals are sodium and potassium.

Compounds of formula (I) wherein $R^1$ is hydrogen and $R^2$ is C(O)$R^7$ contain an assymetric carbon atom. Accordingly, these compounds may be prepared in either optically active form, or as a racemic mixture. Unless otherwise specified, the monoesters of formula (I) described herein are all in the racemic form. However, the scope of the subject invention is not to be considered limited to the racemic form, but to encompass the individual optical isomers of the monoesters of formula (I).

It is to be understood that the definition of $R^5$ together with $R^6$ as keto includes the tautomeric hydroxy form but for convenience the keto form will be used to represent both tautomeric forms.

A preferred group of compounds of formula (I) is that wherein $R^3$ is amino, $R^4$ is hydrogen and $R^5$ together with $R^6$ is keto (compounds of formula (Ia) infra). Another preferred group of compounds of formula (I) is that wherein $R^3$ is amino and $R^6$ is hydrogen, thio or NH$_2$ and $R^4$ together with $R^5$ is a bond. A preferred subgroup within these groups is that wherein $R^1$ and $R^2$ are both —C(O)$R^7$. A more preferred subgroup is that wherein $R^7$ is alkyl of one to five carbon atoms with $R^7$ being methyl or ethyl being most preferred. Another preferred subgroup within these groups is that wherein $R^1$ is hydrogen and $R^2$ is —C(O)$R^7$. A more preferred subgroup within this subgroup is that wherein $R^7$ is alkyl of one to five carbon atoms with $R^7$ being methyl or ethyl being the most preferred.

UTILITY AND ADMINISTRATION

The subject compound of formula (I) and the pharmaceutically acceptable salts thereof exhibit potent antiviral activity when administered to warm blooded and cold blooded animals, particularly mammals, birds, and fish, but most particularly humans. For example, the compound of the present invention exhibits excellent activity against Herpes Simplex virus I and II and related viruses such as cytomegalovirus, Epstein-Barr virus and varicella Zoster virus as well as viral hepatitis such as hepatitis B. Compounds of formula (I) wherein $R^1$ and $R^2$ are —C(O)$R^7$ wherein $R^7$ is ethyl, i.e., the dipropanoate ester exhibits properties which make it particularly suitable for the treatment of viral infections. This ester is more soluble in aqueous solutions than would be expected from the solubility of the adjacent homologs, thus making the dipropanoate ester particularly suitable for parenteral administration. Further, the dipropanoate is more bioavailable.

Pharmaceutical compositions, both veterinary and human, containing the subject compound appropriate for antiviral use are prepared by methods and contain excipients which are well known in the art. A generally recognized compendium of such methods and ingredients is *Remington's Pharmaceutical Sciences* by E. W. Martin, (Mark Publ. Co., 15th Ed., 1975). Liposomes may also be employed as pharmaceutical compositions for the compounds of formula (I), using methods known in the art [for example, as described in Szoka, F. Jr., et al, Ann. Rev. Biophys. Bioeng. 9:467-508 (1980), Schullery, S. E. et al, Biochemistry 19:3919-23 (1980) and Gregoriadin, G. et al, "Liposomes in Biological Systems:", John Wiley and Sons (1980)].

The compound of the invention may be administered parenterally (for example, by intraveneous, subcutaneous, intraperitoneal or intramuscular injection), orally, topically, rectally or intranasally.

The compositions are administered orally or parenterally at dose levels, calculated as the free base, of about 0.1 to 300 mg/kg, preferably 1.0 to 30 mg/kg of mammal body weight, and are used in man in a unit dosage form, administered one to five times daily in the amount of 1 to 500 mg per unit dose. For oral administration, fine powders or granules may contain diluting, dispersing and/or surface active agents, and may be presented in a draught, in water or in a syrup; in capsules or sachets in the dry state or in a non-aqueous solution or suspension, wherein suspending agents may be included; in tablets, wherein binders and lubricants may be included; in a suspension in water or a syrup; or in an aerosol. Where desirable or necessary, flavoring, preserving, suspending, thickening or emulsifying agents may be included. Tablets and granules are preferred, and these may be coated. The amount of compound of formula (I) in the formulation may vary from 0.1 percent weight (% w) to 99% w or more of the compound based on the total formulation and about 1% w to 99.9% w excipient. Preferably the compound is present at a level of 10%-95% w.

For parenteral administration or for administration as drops, as for eye infections, the compounds may be presented in aqueous solution in a concentration of from about 0.1 to 10%, more preferably about 0.1 to 7%. The solution may contain antioxidants, buffers, and other suitable additives.

Alternatively for infections of the eye, or other external tissues, e.g. mouth and skin, the compositions are preferably applied to the infected part of the body of the patient topically as an ointment, cream, aerosol or powder, preferably in an ointment or cream. The compounds may be presented in an ointment, for instance with a water soluble ointment base, or in a cream, for instance with an oil in water cream base, in a concentration of from about 0.01 to 10%; preferably 0.1 to 7%, most preferably about 3.0% w/v. Additionally, viral infections may be treated by use of a sustained release drug delivery system as is described in U.S. Pat. No. 4,217,898.

For aerosol administration, the active ingredient is preferably supplied in finely divided form along with a surfactant and a propellant. Typical percentages of active ingredients are 0.01 to 20% by weight, preferably 0.04 to 1.0%.

Surfactants must, of course, be non-toxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olestearic and oleic acids with an aliphatic polyhydric alcohol or its cyclic anhydride such as, for example, ethylene glycol, glycerol, erythritol, arabitol, mannitol, sorbitol, the hexitol anhydrides derived from sorbitol (the sorbitan esters sold under the trademark "Spans") and the polyoxyethylene and polyoxypropylene derivatives of these esters. Mixed esters, such as mixed or natural glycerides may be employed. The preferred surface-active agents are the oleates or sorbitan, e.g., those sold under the trademarks "Arlacel C" (Sorbitan sesquioleate), "Span 80"(sorbitan monooleate) and "Span 85"(sorbitan trioleate). The surfactant may constitute 0.1-20% by weight of the composition, preferably 0.25-5%.

The balance of the composition is ordinarly propellant. Liquefied propellants are typically gases at ambient conditions, and are condensed under pressure. Among suitable liquefied propellants are the lower alkanes containing up to five carbons, such as butane and propane; and preferably fluorinated or fluorochlorinated alkanes, such as are sold under the trademark "Freon." Mixtures of the above may also be employed.

In producing the aerosol, a container equipped with a suitable valve is filled with the appropriate propellant, containing the finely divided active ingredient and surfactant. The ingredients are thus maintained at an elevated pressure until released by action of the valve.

The compounds of the present invention or compositions containing same are also useful in treating non-human mammals, birds, e.g., chickens and turkeys, and cold-blooded animals, e.g., fish. For example, the compounds of the present invention and compositions containing same exhibit antiviral activity against the following non-human viruses:
Sciruid herpesvirus 1
Cavlid herpesvirus 1
Lagomorph herpesvirus 1
Phasianid herpesvirus 1
Phasianid herpesvirus 2 (Marek's disease)
Turkey herpesvirus 1
Anatid herpesvirus 1
Catfish herpesvirus 1
Equid herpesvirus 3
Bovid herpesvirus 1
Bovid herpesvirus 2
Bovid herpesvirus 3
Bovid herpesvirus 4
Pig herpesvirus 1
Pig herpesvirus 2
Murid herpesvirus 1
Cebid herpesvirus 1
Cebid herpesvirus 2
Tupaiid herpesvirus 1
Canine herpesvirus 1
Feline herpesvirus 1
Equid herpesvirus 1
Equid herpesvirus 2

Avian viral diseases such as Marek's disease and the like are prevented and/or treated by compounds of the present invention by methods well-known in the veterinary art such as by injecting the birds with the composition containing the compound, or by adding the compound of the instant invention to feed or drinking water.

Fish which are in a confined area such as a pool, aquarium or holding tank may also be treated for viral infections such as herpeslike viruses, e.g., channel catfish virus (CCV), herpes-virus salomones, Nerka virus and the like by adding the compound directly to the water of the pool, aquarium or holding tank or by incorporating the compounds into the feed.

The exact regimen for administration of the compounds and compositions disclosed herein will necessarily be dependent upon the needs of the individual subject being treated, the type of treatment and, of course, the judgement of the attending practitioner.

PREPARATION

The compounds of formula (I) may be prepared from compounds of formula (X) (infra) and compounds of formula (XIV) wherein A is hydrogen (infra) which compounds are prepared by Reaction Sequence Ib. Intermediate of formula (V), which is used in Reaction Sequence Ib, is prepared by Reaction Sequence Ia.

Reaction Sequence Ia

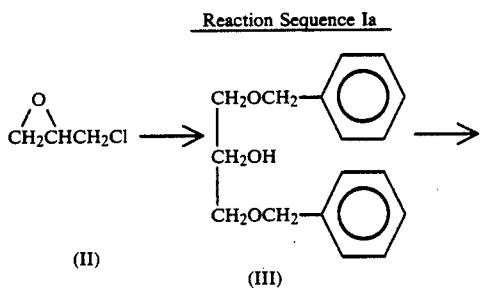

-continued
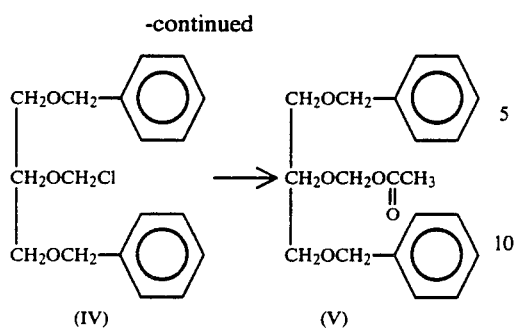
Reaction Sequence Ib
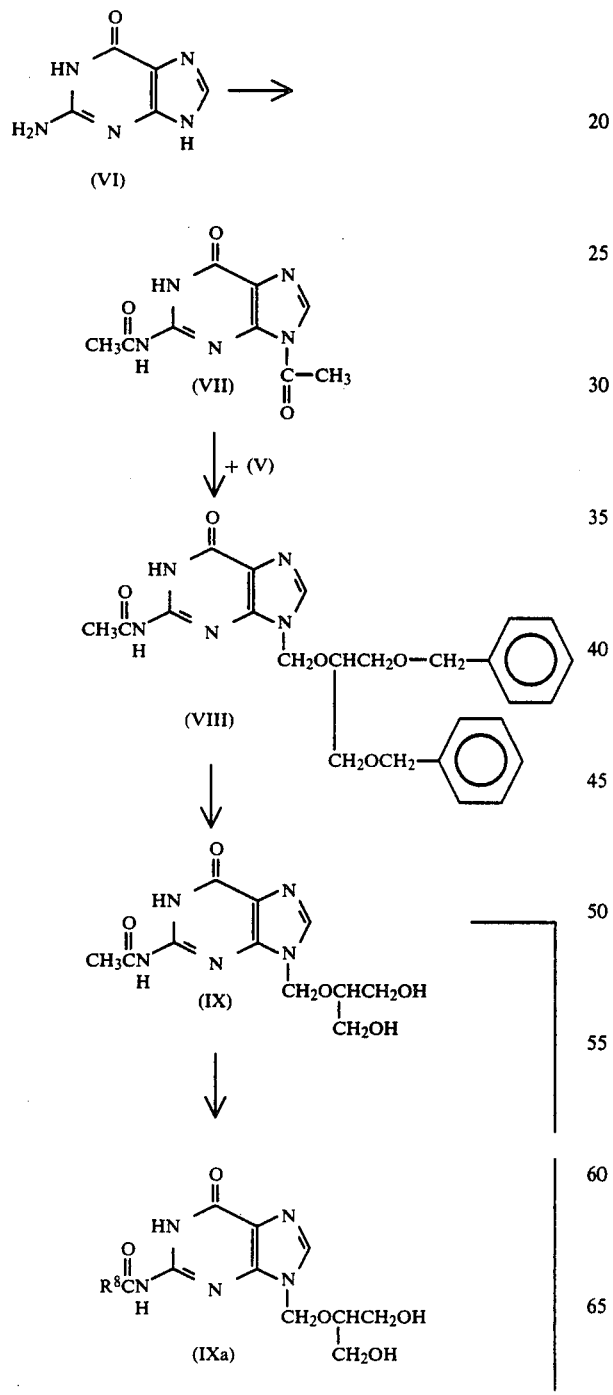
-continued
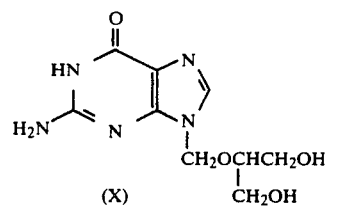
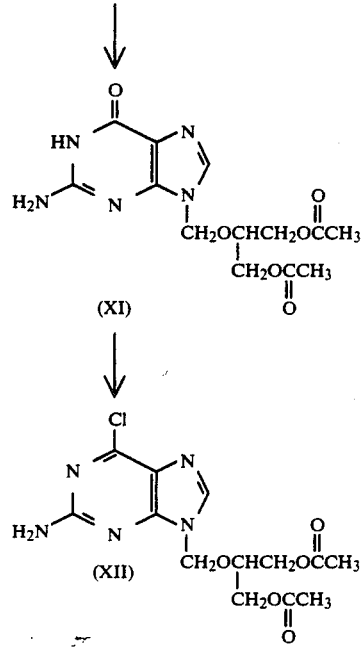
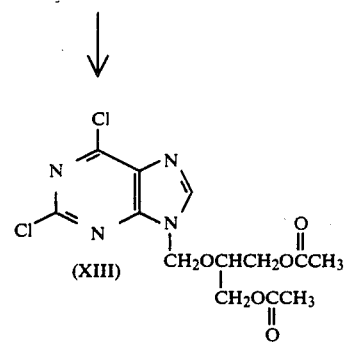
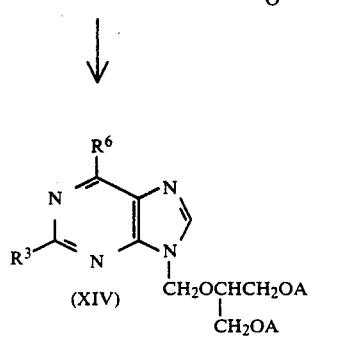
wherein A is hydrogen or acetyl and $R^3$ and $R^6$ are defined in the following table:

|     | $R^3$  | $R^6$  |
| --- | ------ | ------ |
| (a) | $NH_2$ | $OR$   |
| (b) | $NH_2$ | $SH$   |
| (c) | $N_3$  | $N_3$  |
| (d) | $NH_2$ | $NH_2$ |
| (e) | $Cl$   | $NH_2$ |
| (f) | $N_3$  | $NH_2$ |
| (g) | $NH_2$ | $H$    |
| (h) | $H$    | $NH_2$ |
| (i) | $H$    | $SH$   |
| (j) | $SH$   | $NH_2$ |

In Reaction Sequence Ia, the compound of formula (III) is prepared by adding epichlorohydrin (II) dropwise to a solution of an alkali metal salt, preferably the sodium salt, of optionally substituted benzyl alcohol in a solvent such as dimethylformamide, dimethylacetamide, hexamethylphosphoramide, dimethylsulfoxide, sulfolane, tetrahydrofuran, and dioxane at a temperature of about 0° C. to 100° C., preferably at about 15° C. to 40° C. The reaction mixture is stirred for about 10 hours to 24 hours, preferably for about 12 hours to 18 hours at a temperature of about 0° C. to 100° C., preferably from about 20° C. to 50° C.

Compound of formula (III) is chloromethylated to compound of formula (IV) by bubbling dry hydrogen chloride gas in a solution of the compound and paraformaldehyde dissolved in a halogenated hydrocarbon solvent such as dichloroethane, chloroform, dichloromethane, or 1,1,2-trichloroethane cooled to a temperature of about 0° C. to 25° C., preferably at a temperature of about 0° C. The hydrogen chloride gas is added over 30 minutes to 3 hours, preferably over 1 hour to 2 hours until the paraformaldehyde dissolves. The solution is held at a temperature from about 0° C. to 10° C. for about 12 hours to 48 hours, preferably from about 0° to 5° C. for about 16 hours to 24 hours.

Compound of formula (V) is prepared by reacting an alkali metal acetate such as sodium acetate with compound of formula (IV) dissolved in a solvent such as dimethylformamide, tetrahydrofuran, dimethylacetamide, hexamethylphosphoramide, dimethylsulfoxide, sulfolane, and dioxane at a temperature of about 0° C. to 45° C., preferably from about 0° C. to 25° C. The solution is stirred from about 5 to about 24 hours, preferably from about 10 hours to about 18 hours at a temperature of about 10° C. to about 30° C., preferably at a temperature of about 15° C. to 25° C.

In Reaction Sequence Ib, compound of formula (VII) is prepared by heating guanine (VI) with acetic anhydride, neat, at reflux for about 10 to 24 hours, preferably for about 12 to 18 hours.

$N^2$,9-Diacetylguanine of formula (VII) is reacted with compound of formula (V) to form compound of formula (VIII) neat or in a solvent such as dioxane, sulfolane and the like in the presence of a catalytic amount of an acid such as bis(p-nitrophenyl)phosphate, toluenesulfonic acid, methylphosphonic acid or dichloroacetic acid, preferably bis(p-nitrophenyl)phosphate at a temperature of about 75° C. to 200° C., preferably at about 110° C. to 180° C. The reaction is generally carried out using 0.8 moles to 1.2 moles of compound of formula (V) to one mole of compound of formula (VII).

The benzyl protecting groups are removed from compound of formula (VIII) by catalytic hydrogenation to form compound of formula (IX). A catalyst such as palladium on carbon in a slurry is added to a solution of compound of formula (VIII) dissolved in a solvent such as aqueous methanol. Hydrogen is added to the solution at a pressure of 15 psi to 200 psi, preferably at a pressure of 30 psi to 80 psi.

Compound of formula (X) is prepared by deacetylating compound of formula (IX) with a base such as ammonia dissolved in an alcohol such as methanol. A solution of compound of formula (IX) and the base is stirred for about 5 hours to 36 hours, preferably for about 10 hours to 24 hours at a temperature of about 10° C. to 30° C., preferably at a temperature of about 15° C. to 25° C.

Compound of formula (X) may be esterified to the diacetate of formula (XI) by reacting compound of formula (X) with excess acetic anhydride, either neat or in a solvent such as dimethylformamide, dimethylacetamide and the like at room temperature for two to three days.

Compound of formula (XII) may be prepared by reacting compound of formula (XI) with phosphorus oxychloride according to the method described in J. Org. Chem. 28:945, 1963. Compound of formula (XI) is added to a solution of phosphorus oxychloride in N,N-diethylaniline at room temperature. The suspension is heated at reflux for 2 to 30 minutes, preferably from 2 to 5 minutes. The excess phosphorus oxychloride is removed and the product recovered by conventional means such as extraction with an organic solvent followed by chromatography.

Compound of formula (XII) may be further chlorinated by forming the diazo salt with sodium nitrite in hydrochloric acid as described in J. Org. Chem. 31:3258, 1966. To compound of formula (XII) in aqueous hydrochloric acid is added sodium nitrite in water at 0° to 5° C. The solution is diluted with water and the excess hydrochloric acid is neutralized with aqueous ammonia and compound of formula (XIII) is recovered by methods well known in the art such as extraction with an organic solvent followed by chromatography.

Compounds of formula (XIV) may be prepared from compounds of formulas (XII) and (XIII) by methods well known in the art. See, for example, "Heterocyclic Compounds—Fused Pyrimidines Part II Purines, Ed. D. J. Brown (1971) Wiley-Interscience" and U.S. Pat. No. 4,199,574 which patent is incorporated herein by reference. See preceding table for compounds of formula (XIV)a-j.

Compound of formula (XIVb) wherein A is hydrogen may be prepared by reacting a compound of formula (XII) with thiourea dissolved in a solvent such as isopropanol with heating at reflux for one to two hours. The thiourea adduct which forms is broken down with an alkali such as aqueous ammonia yielding the thio compound. The reaction also leads to the hydrolysis of the ester groups.

Compounds of formula (XIVa) wherein A is hydrogen and R is lower alkyl are prepared from compound of formula (XII) by treatment with an alcoholic solution of the appropriate alkali metal alkoxide such as sodium methoxide in methanol at room temperature or with mild heating.

Various compounds of formula (XIV) may be prepared from compound of formula (XIII). For example, compound of formula (XIVc) wherein A is acetyl is prepared by treating compound of formula (XIII) with sodium azide in a solvent such as ethanol:water, dimethylformamide, hexamethylphosphoramide and the like. The reactants are heated for two to 24 hours at 80° to 200° C. Compound of formula (XIVd), wherein A is hydrogen, are prepared by hydrogenating compound of formula (XIVc) using, for example, a palladium on charcoal catalyst.

Compound of formula (XIII) is converted to compound of formula (XIVe) wherein A is hydrogen by heating compound of formula (XIII) and ammonia dissolved in methanol in a bomb for 16 to 24 hours at 85° to 110° C. The above compound may be further ammoniated by heating compound of formula (XIVe) dissolved in liquid ammonia in a bomb for 24 to 48 hours at 110° to 150° C. to form compound of formula (XIVd) wherein A is hydrogen.

Another method of preparing compound of formula (XIVd) is by treating compound of formula (XIVe) with hydrazine and then with a cold solution of sodium nitrite to form compound of formula (XIVf) wherein A is hydrogen, which in turn is hydrogenated to the compound of formula (XIVd) using, for example, a palladium on charcoal catalyst.

The amino groups of compounds of formula (XIV) wherein $R^3$ and/or $R^6$ is amino may be alkylated to the secondary or tertiary amines by treatment with an alkyl halide such as methyl iodide. A preferred method for preparing the above alkylated amino compounds is by reacting a compound of formula (XIII) or (XIVe) with an alkyl or dialkyl amine.

Compounds of formula (IXa) wherein $R^8$ is other than methyl may be prepared by protecting the hydroxy groups of compound of formula (IX) with a trityl protecting agent as defined infra, deacetylating the amino nitrogen, reacting the deacetylated compound with the appropriate acid chloride and removing the protecting groups with glacial acetic acid:water.

Those compounds of formula (XIV) wherein A is acetyl may be hydrolyzed by methods well known in the art such as by acidic or basic hydrolysis.

Compounds of formulas (XIVg) and (XIVh) may be prepared by the hydrogenation of compounds of formulas (XII) and (XIVe) respectively using a hydrogenation catalyst such as palladium in the presence of a base such as magnesium dioxide.

Compound of formula (XIVi) wherein A is hydrogen is prepared by reacting compound of formula (XIVh) with sodium nitrite in acetic acid to form the 6-keto compound which in turn is chlorinated with a chlorinating agent such as phosphoryl chloride, phosphorous pentachloride and the like by methods well known in the art. The 6-chloro intermediate is treated with thiourea as described above.

Compounds of formula (XIVj) may be prepared, for example, by reacting compound of formula (XIVe) with methanolic hydrogen sulfide-ammonium carbonate as described in J. Org. Chem., 39(9):1256, 1974 or with sodium mercaptide in dimethylformamide as described in J. Med. Chem., 16(12):1381, 1973.

Compounds of formula (XIV) wherein $R^3$ or $R^6$ is thio may be alkylated with an alkyl halide such as an alkyl iodide in a solvent such as an alkanol at room temperature.

The following compounds of formula (XIV) wherein A is hydrogen, for example, may be prepared by one or a combination of the methods discussed above:

2-amino-6-methoxy-9-(1,3-dihydroxy-2-propoxymethyl)purine;
2-methylamino-6-ethoxy-9-(1,3-dihydroxy-2-propoxymethyl)purine;
2-amino-6-thio-9-(1,3-dihydroxy-2-propoxymethyl)purine, m.p. 155°-157° C.;
2-n-butylamino-6-thio-9-(1,3-dihydroxy-2-propoxymethyl)purine;
2-amino-6-methylthio-9-(1,3-dihydroxy-2-propoxymethyl) purine;
2-dimethylamino-6-methylthio-9-(1,3-dihydroxy-2-propoxymethyl)purine;
2,6-diazido-9-(1,3-dihydroxy-2-propoxymethyl)purine;
2,6-diamino-9-(1,3-dihydroxy-2-propoxymethyl)purine, m.p. 174°-180° C.;
2-methylamino-6-amino-9-(1,3-dihydroxy-2-propoxymethyl)purine;
2-amino-6-methylamino-9-(1,3-dihydroxy-2-propoxymethyl)purine;
2,6-di(methylamino)-9-(1,3-dihydroxy-2-propoxymethyl)purine;
6-chloro-2-amino-9-(1,3-dihydroxy-2-propoxymethyl)purine, m.p. 197.5°-198.5° C.;
2-chloro-6-methylamino-9-(1,3-dihydroxy-2-propoxymethyl)purine;
2-azido-6-ethylamino-9-(1,3-dihydroxy-2-propoxymethyl)purine
2-amino-9-(1,3-dihydroxy-2-propoxymethyl)purine;
2-methylamino-9-(1,3-dihydroxy-2-propoxymethyl)purine;
2-dimethylamino-9-(1,3-dihydroxy-2-propoxymethyl)purine;
6-amino-9-(1,3-dihydroxy-2-propoxymethyl)purine;
6-methylamino-9-(1,3-dihydroxy-2-propoxymethyl)purine;
6-dimethylamino-9-(1,3-dihydroxy-2-propoxymethyl)purine;
6-thio-9-(1,3-dihydroxy-2-propoxymethyl)purine;
6-methylthio-9-(1,3-dihydroxy-2-propoxymethyl)purine; and
6-amino-2-thio-9-(1,3-dihydroxy-2-propoxymethyl)purine.

Diesters of formula (I) may be prepared by esterification methods well known in the art. For example, diesters of formula (I) wherein $R^7$ is lower alkyl may be prepared by reacting compounds of formula (X) and (XIV) wherein A is hydrogen with an excess of the appropriate acid anhydride, either neat or in a solvent such as dimethylformamide, dimethylacetamide, N-methylpyrrolidine and the like. The reactants are stirred for one to five days, preferably for two to three days at 0° to 50° C., preferably at room temperature in the presence of a catalyst, e.g., 4-dimethylaminopyridine. Compounds of formula (X) or (XIV) and the acid anhydride are in a molar ratio of approximately 1:10–100.

The acid anhydrides are readily available or if not readily available may be prepared by methods well known in the art such as by heating the acid in the presence of acetic anhydride or acetyl chloride.

The diesters of formula (I) wherein $R^7$ is hydrogen may be prepared by the above described method using the mixed anhydride of formic acid and acetic acid, which may be prepared by reacting formic acid with acetic anhydride, neat, at 0° to 40° C.

Another method for preparing the diesters of formula (I) for all values of $R^7$ is by first treating compound of formula (XI) or (XIV) wherein A is acetyl and $R^3$ and/or $R^6$ is amino with a trityl protecting agent such as triphenylmethyl chloride (trityl chloride), 4-methoxyphenyldiphenylmethyl chloride (mono-methoxytrityl-chloride) and the like. The trityl protecting agents are readily available from, i.a., Aldrich Chemical Co. The reactants in a solvent such as dimethylformamide, pyridine, and the like with a catalyst e.g., 4-dimethylpyridine are heated at 40° to 70° C., preferably at 45° to 60° C. for 8 to 24 hours, preferably for 12 to 18 hours. The amino protected compound is isolated by conventional means such as crystallization and the acetate groups are hydrolyzed with a base, such as an alkali metal hydroxide, e.g., sodium hydroxide and potassium hydroxide, or with ammonium hydroxide. The dihydroxy compound and a catalyst such as 4-dimethylaminopyridine in pyridine is added dropwise to the appropriate acid chloride either neat or in a solvent such as methylene chloride, dichloroethane and the like. The reactants are stirred at room temperature for 10 to 24 hours, preferably from 12 to 18 hours. The product is isolated by methods well known in the art such as chromatography. The amino protective groups are removed by treatment with an organic acid such as glacial acetic acid, trifluoroacetic acid and the like with heating from 60° to 100° C., preferably from 60° to 80° C. for one to twelve hours, preferably from one to five hours. The product is isolated by chromatography or crystallization.

The amino group(s) of the above described compound of formulas (XI) and (XIV) may also be protected by reacting the compounds with the acetal of N,N-dimethyl formamide available from, i.a., Aldrich Chemical Co. and then proceeding as discussed above.

The acid chlorides are readily available or if not readily available may be prepared by reacting the appropriate acid with a chlorinating agent such as phosphorus trichloride, phosphorus pentachloride, or thionyl chloride under reaction conditions well known in the art.

Diesters of formula (I) wherein $R^3$ is amino, $R^5$ together with $R^6$ is keto and $R^4$ is hydrogen and $R^7$ is alkyl of seven to nineteen carbon atoms, alkenyl of seven to nineteen carbon atoms, 2-methyl-2-propyl, 1-adamantyl or phenyl may also be prepared by esterifying with the appropriate acid chloride. The acid chloride dissolved in a solvent such as methylene chloride, dichloroethane and the like is added to compound of formula (IX) dissolved in a solvent such as pyridine, lutidines and the like. The reactants are stirred for 9 to 24 hours, preferably for 16 to 24 hours at 15° to 50° C., preferably at room temperature. The amino group is deacetylated by treatment with an alcoholic solution of a base such as a methanol solution of ammonium hydroxide.

Another method for preparing diesters of formula (I) wherein $R^7$ is alkyl of seven to nineteen carbon atoms is by reacting compounds of formulas (X) or (XIV) wherein A is hydrogen with the condensation product of dicyclohexylcarbodiimide, available from Aldrich Chemical Co., and the appropriate carboxylic acid. The carboxylic acid in a molar excess of dicyclohexylcarbodiimide is added to the above compounds dissolved in a solvent such as dimethylformamide, dimethylacetamide and the like. The solution is stirred with heating from 35° to 75° C., preferably from 40° to 60° C. for 16 to 72 hours, preferably for 24 to 60 hours. The diesters of formula (I) are isolated by precipitation.

Diesters and monoesters of formula (I) wherein $R^7$ is an hydroxyalkyl are prepared by first protecting the hydroxy group of the hydroxy acid with a benzyl group, reacting the protected acid with a trityl protected compound of formula (X) or (XIV), as described infra, wherein A is hydrogen and removing the benzyl group by catalytic hydrogenation followed by removal of the trityl group(s) as discussed above.

The monoester of formula (I) may be prepared by reacting compounds of formula (X) or (XIV) wherein A is hydrogen with a trityl protective group as defined supra. The protective group reacts with the amino nitrogen if present and one hydroxy group. The unprotected hydroxy group is esterified using an acid chloride by the method described supra. The protective groups are removed as described herein above.

The following specific description is given to enable those skilled in the art to more clearly understand and practice the invention. It should not be considered as a limitation upon the scope of the invention but merely as being illustrative and representative thereof.

PREPARATION I

Preparation of 1,3-Di-O-benzylglycerol

Sodium hydride (100 g (50% dispersion in mineral oil), 2.08 mol) was washed twice with 1 l of hexane then dried under nitrogen. Dry dimethylformamide (1.5 l) was added. Benzyl alcohol (400 ml) was then added at such a rate to keep the temperature below 50° C. The addition took 2 hours. Epichlorohydrin (92.5 g, 1 mol) was then added dropwise over 0.5 hour with ice cooling in order to keep the temperature below 40° C. The solution was next stirred for 16 hours at 21° C. then for 2.5 hours at 50° C. The dimethylformamide was then removed by evaporation at reduced pressure. The oily residue was dissolved in 2.5 l diethyl ether. The organic solution was washed with 2 l of water, 2 l of 2% hydrochloric acid, 2 l of 1% sodium bicarbonate, and 1 l of brine, dried over sodium sulfate, and concentrated to a brown oil. Distillation gave 147.8g of 1,3-di-O-benzylglycerol (bp 170°–180° C./1 torr).

PREPARATION II

Preparation of 1,3-Di-O-benzyl-2-O-chloromethylglycerol

Dry hydrogen chloride gas was bubbled for 1.5 hours into a solution of 1,3-di-O-benzylglycerol from Preparation I (15 g, 55 mmol) and paraformaldehyde (3.3 g, 110 mmol) in 175 ml of 1,2-dichloroethane at 0° C. The solution was then stored in a stoppered flask for 21 hours at 4° C. Next, the solution was dried over magnesium sulfate with warming to 21° C. then filtered and concentrated to give 17.5 g of 1,3-di-O-benzyl-2-O-chloromethylglycerol.

PREPARATION III

Preparation of 2-O-Acetoxymethyl-1,3-di-O-benzylglycerol

To a solution of 1,3-di-O-benzyl-2-O-chloromethylglycerol from Preparation II (17.5 g, 55 mmol) in 400 ml of dimethlyformamide at 0° C. under a drying tube was added sodium acetate (6 g). The solution was then warmed to 21° C. and magnetically stirred for 15 hours. The solvent was removed by evaporation at reduced pressure and the oily residue dissolved in 1 pound of diethylether. The ether solution was washed once with 750 ml of water, two times with 250 ml of water, and once with 250 ml of brine, dried over sodium sulfate and concentrated to give 19 g of 2-O-acetoxymethyl-1,3-di-O-benzylglycerol as an oil.

PREPARATION IV

Preparation of $N^2$,9-Diacetylguanine

Guanine (20 g, 0.132 mol) was combined with 300 ml of acetic anhydride and the mixture heated at reflux for 16 hours. The mixture was cooled and the excess acetic anhydride removed by evaporation at reduced pressure. The residue was recrystallized from dimethyl sulfoxide to give 25.6 g of $N^2$,9-diacetylguanine.

PREPARATION V

A. Preparation of $N^2$-Acetyl-9-(1,3-dibenzyloxy-2-propoxymethyl)guanine $N^2$,9-Diacetylguanine from Preparation IV (15.61 g, 66 mmol), 2-O-acetoxymethyl-1,3-di-O-benzylglycerol from Preparation III (19 g, 55 mmol), and bis(p-nitrophenyl)phosphate (0.5 g) were stirred together with 150 ml of diethylether. The solvent was removed by evaporation and the residue heated in a 175° C. oil bath for 1.5 hours under a stream of nitrogen. Column chromatography eluting with 1:9 methanol/methylene chloride followed by recrystallization from ethyl acetate afforded 4.76 g of $N^2$-acetyl-9-(1,3-dibenzyloxy-2-propoxymethyl)guanine, mp 145°–146° C.

B. Preparation of $N^2$-Acetyl-9-(1,3-dihydroxy-2-propoxymethyl)guanine

To a solution of $N^2$-acetyl-9-(1,3-dibenzyloxy-2-propoxymethyl)guanine (4.62 g, 9.67 mmol) in 150 ml of methanol plus 40 ml of water was added 20% palladium hydroxide on carbon as a slurry in 10 ml of water. The mixture was hydrogenated on a Parr hydrogenator at 60 psi of hydrogen for 38 hours then filtered through celite and concentrated to a white solid. Recrystallization from methanol/ethyl acetate gave 1.4 g of $N^2$-acetyl-9-(1,3-dihydroxy-2-propoxymethyl)guanine, mp 205°–208° C.

The mother liquor was further reduced with 10% palladium on carbon (1 g) in 150 ml of methanol plus 50 ml of water at 60 psi for 47 hours. The total yield of $N^2$-acetyl-9-(1,3-dihydroxy-2-propoxymethyl)guanine was 2.11 g.

C. Preparation of 9-(1,3-Dihydroxy-2-propoxymethyl)guanine $N^2$-Acetyl-9-(1,3-dihydroxy-2-propoxymethyl)guanine (721.9 mg, 2.4 mmol) was stirred with 50 ml of methanolic ammonia solution (methanol saturated with ammonia at 0° C.) for 17 hours at 21° C. The solution was concentrated to a white solid and the residue recrystallized from water or methanol to give 582.3 mg of 9-(1,3-dihydroxy-2propoxymethyl)guanine, mp 250° C.

EXAMPLE 1

9-(1,3-Diacetyloxy-2-propoxymethyl)guanine (Compound wherein $R^1$ and $R^2$ are acetyl, $R^3$ is amino, $R^4$ is hydrogen and $R^5$ and $R^6$ are keto)

A mixture of 3.00 g of 9-(1,3-dihydroxy-2-propoxymethyl)guanine, 300 mg of 4-dimethylaminopyridine, and 100 ml of acetic anhydride was vigorously stirred for 3 days at room temperature. The acetic anhydride was removed by evaporation at reduced pressure and the residue recrystallized from methanol to give 3.62 g of 9-(1,3-diacetyloxy-2-propoxymethyl)guanine, m.p. 237°–239°.

EXAMPLE 2

9-(1,3-(2,2-dimethvlpropanoyloxy)-2-propoxymethyl)guanine (Compound wherein $R^1$ and $R^2$ are 2,2-dimethylpropanoyl, $R^3$ is amino, $R^4$ is hydrogen, and $R^5$ and $R^6$ are keto)

A mixture of 1.306 g of 9-(1,3-dihydroxy-2-propoxymethyl)guanine, 150 mg of 4-dimethylaminopyridine, and 50 ml of 2,2-dimethylpropanoic acid anhydride and dry dimethylformamide (75 ml) was vigorously stirred for 2 days. The dimethylformamide was removed by evaporation at reduced pressure, and 200 ml of ethyl ether were added to the residue. After cooling to 0° C., the precipitate was isolated by filtration and recrystallized from methanol to give 1.83 g of 9-(1,3-di-(2,2-dimethylpropanoyloxy)-2-propoxymethyl)guanine, m.p. 230°–232°.

Similarly, using the procedure in Example 1 or 2, substituting the appropriate acid anhydride for acetic anhydride or 2,2-dimethylpropanoic acid anhydride and using compound of Formula (X) or the appropriate compound of formula (XIV) wherein A is hydrogen the following compounds, for example, are prepared:

2-amino-6-methoxy-9-(1,3-diacetyloxy-2-propoxymethyl)purine;
2-methylamino-6-ethoxy-9-(1,3-dipropanoyloxy-2-propoxymethyl)purine;
2-amino-6-thio-9-(1,3-di-acetyloxy-2-propoxymethyl)purine, m.p. 235°–236.5° C.;
2-n-butylamino-6-thio-9-(1,3-di-n-pentanoyloxy-2-propoxymethyl)purine;
2-amino-6-methylthio-9-[1,3-di-2-methylpropanoyloxy)2-propoxymethyl]purine;
2-dimethylamino-6-methylthio-9-[1,3-di-(2,2-dimethylpropanoyloxy)-2-propoxymethyl]purine;
2,6-diazido-9-(1,3-di-n-hexanoyloxy-2-propoxymethyl)purine;
2,6-diamino-9-(1,3-diacetyloxy-2-propoxymethyl)purine;
2-methylamino-6-amino-9-(1,3-dipropanoyloxy-2-propoxymethyl)purine;
2-amino-6-methylamino-9-(1,3-di-n-butanoyloxy-2-propoxymethyl)purine;
2,6-di(methylamino)-9-[1,3-di-(2-methylpropanoyloxy)2-propoxymethyl]purine;
6-chloro-2-amino-9-[1,3-diacetyloxy-2-propoxymethyl]purine, m.p. 122°–123° C.;
2-chloro-6-methylamino-9-(1,3-di-n-pentanoyloxy-2-propoxymethyl)purine;
2-azido-6-ethylamino-9-(1,3-di-n-hexanoyloxy-2-propoxymethyl)purine;
2-amino-9-[1,3-di-(1-adamantylcarboxy)-2-propoxymethyl]purine;
2-methylamino-9-(1,3-dipropanoyloxy-2-propoxymethyl)purine;
2-dimethylamino-9-(1,3-di-n-butanoyloxy-2-propoxymethyl)purine;
6-amino-9-[1,3-di-(2-methylpropanoyloxy)-2-propoxymethyl]purine;
6-methylamino-9-(1,3-di-n-pentanoyloxy-2-propoxymethyl)purine;
6-dimethylamino-9-[1,3-di-(2,2-dimethylpropanoyloxy)2-propoxymethyl]purine;
6-thio-9-(1,3-di-n-hexanoyloxy-2-propoxymethyl)purine;

6-methylthio-9-(1,3-diacetyloxy-2-propoxymethyl)purine;

9-(1,3-dipropanoyloxy-2-propoxymethyl)guanine, m.p. 191°-193° C.;

9-(1,3-di-n-butanoyloxy-2-propoxymethyl)guanine, m.p. 199°-201° C.;

9-[1,3-di-(2-methylpropanoyloxy)-2-propoxymethyl]-guanine;

9-(1,3-di-n-pentanoyloxy-2-propoxymethyl)guanine, m.p. 193°-198° C.;

9-(1,3-di-n-hexanoyloxy-2-propoxymethyl)guanine, m.p. 179°-181° C.;

9-[1,3-di-(4-methylpentanoyloxy)-2-propoxymethyl]-guanine, m.p. 185.5°-186.5° C.;

9-(1,3-di-methoxyacetyloxy-2-propoxymethyl)guanine, m.p. 183°-185° C.; and

9-[1,3-di-(3-carboxypropanoyoxy)-2-propoxymethyl]-guanine, m.p. 140°-144° C.

EXAMPLE 3

9-(1,3-Di-n-hexadecanoyloxy-2-propoxymethyl)guanine

To 50 mg of 9-(1,3-dihydroxy-2-propoxymethyl)guanine in 5 ml of N,N-dimethylformamide were added 290 mg dicyclohexycarbodiimide and 300 mg of n-hexadecanoic acid and the solution was stirred at 50° C. for 50 hours. The compound was then precipitated in ice water. The water was extracted with methylene chloride (3x). The combined methylene chloride extracts were concentrated, then purified on preparative silica gel plates developed in 1:9 methanol:methylene chloride to yield 140 mg 9-(1,3-di-n-hexadecanoyloxy-2-propoxymethyl)guanine, m.p. 150°-154° C.

Similarly, proceeding as in the above example, substituting the appropriate carboxylic acid for n-hexadecanoic acid and using compound of formula (X) or compounds of formula (XIV) wherein A is hydrogen, the following compounds, for example, are prepared:

2-amino-6-methoxy-9-(1,3-di-n-heptanoyloxy-2-propoxymethyl)-purine;

2-amino-6-chloro-9-(1,3-di-n-octanoyloxy-2-propoxymethyl)purine;

2-amino-6-thio-9-(1,3-di-n-decanoyloxy-2-propoxymethyl)purine;

2-n-butylamino-6-thio-9-(1,3-di-n-dodecanoyloxy-2-propoxymethyl)purine;

2-amino-6-methylthio-9-(1,3-di-n-tetradecanoyloxy-2-propoxymethyl)purine;

2-dimethylamino-6-methylthio-9-(1,3-di-n-hexadecanoyloxy-2-propoxymethyl)purine;

2,6-diazido-9-(1,3-di-n-octadecanoyloxy-2-propoxymethyl)purine;

2,6-diamino-9-(1,3-di-n-eicosanoyloxy-2-propoxymethyl)purine;

2-methylamino-6-amino-9-(1,3-di-n-nonanoyloxy-2-propoxymethyl)purine;

2-amino-9-(1,3-di-n-octanoyloxy-2-propoxymethyl)purine;

2,6-di(methylamino)-9-(1,3-di-n-decanoyloxy-2-propoxymethyl)purine;

2-chloro-6-amino-9-(1,3-di-n-dodecanoyloxy2-propoxymethyl)purine;

2-chloro-6-methylamino-9-(1,3-di-n-tetradecanoyloxy-2-propoxymethyl)purine;

2-azido-6-ethylamino-9-(1,3-di-n-hexadecanoyloxy-2-propoxymethyl)purine;

6-amino-9-(1,3-di-n-octadecanoyloxy-2-propoxymethyl)purine;

2-methylamino-9-(1,3-n-eicosanoyloxy-2-propoxymethyl)purine;

2-dimethylamino-9-(1,3-di-n-nonanoyloxy-2-propoxymethyl)purine;

2-amino-9-(1,3-di-n-octanoyloxy-2-propoxymethyl)purine;

6-methylamino-9-(1,3-di-n-decanoyloxy-2-propoxymethyl)purine;

6-dimethylamino-9-(1,3-di-n-dodecanoyloxy-2-propoxymethyl)purine;

6-thio-9-(1,3-di-n-tetradecanoyloxy-2-propoxymethyl)purine;

6-methylthio-9-(1,3-di-n-hexadecanoyloxy-2-propoxymethyl)purine;

9-(1,3-di-n-nonanoyloxy-2-propoxymethyl)guanine;

9-(1,3-di-n-octanoyloxy-2-propoxymethyl)guanine, m.p 165°-166° C.;

9-(1,3-di-n-decanoyloxy-2-propoxymethyl)guanine, m.p. 158°-160° C.;

9-(1,3-di-n-dodecanoyloxy-2-propoxymethyl)guanine, m.p. 162°-164° C.;

9-(1,3-di-n-tetradecanoyloxy-2-propoxymethyl)guanine, m.p. 137°-140° C.;

9-(1,3-di-n-octadecanoyloxy-2-propoxymethyl)guanine; and 9-(1,3-di-n-eicosanoyloxy-2-propoxymethyl)guanine.

EXAMPLE 4

A.

$N^2$-(4-methoxyphenyldiphenylmethyl)-9-(1,3-diacetoxy-2-propoxymethyl)guanine

A solution of 3.3 g of 9-(1,3-diacetoxy-2-propoxymethyl)guanine, 7.0 g of 4-methoxyphenyldiphenylmethyl chloride, 7.0 ml of triethylamine and 300 mg of 4-dimethylaminopyridine in 50 ml of dry dimethylformamide was heated with magnetic stirring at 50° C. for 15 hours. Methanol (5 ml) was added. The solution was then concentrated at reduced pressure to a brown oil which was chromatographed over silica gel eluting with 1:12 methanol:methylene chloride to give an oil. The oil was crystallized from ethyl acetate:hexane to give 5.42 g of $N^2$-(4-methoxyphenyldiphenylmethyl)-9-(1,3-diacetoxy-2-propoxymethyl)guanine, m.p. 139°-141°.

Triphenylmethyl chloride may be substituted for 4-methoxyphenyldiphenylmehtyl chloride in part A above to prepare the corresponding triphenylmethyl protected compounds.

Similarly proceeding as above in Part A, substituting the appropriate compound of formula (XIV) wherein A is acetyl, the following compounds, for example, are prepared:

2-(4-methoxyphenyldiphenylmethylamino)-6-methoxy-9-(1,3-diacetyloxy-2-propoxymethyl)purine;

2-(4-methoxyphenyldiphenylmethylamino)-6-thio-9-(1,3-diacetyloxy-2-propoxymethyl)purine;

2-(4-methoxyphenyldiphenylmethylamino)-6-methylthio-9-(1,3-diacetyloxy-2-propoxymethyl)purine;

2,6-di-(4-methoxyphenyldiphenylmethylamino)-9-(1,3-diacetyloxy-2-propoxymethyl)purine;

2-methylamino-6-(4-methoxyphenyldiphenylmethylamino)-9-(1,3-diacetyloxy-2-propoxymethyl)purine;

2-(4-methoxyphenyldiphenylmethylamino)-9-(1,3-diacetyloxy-2-propoxymethyl)purine;

6-chloro-2-(4-methoxyphenyldiphenylmethylamino)-9-(1,3-diacetyloxy-2-propoxymethyl)purine;
2-(4-methoxyphenyldiphenylmethylamino)-9-(1,3-diacetyloxy-2-propoxymethyl)purine; and
6-(4-methoxyphenyldiphenylmethylamino)-9-(1,3-diacetyloxy-2-propoxymethyl)purine.

B.
$N^2$-(4-methoxyphenyldiphenylmethyl)-9-(1,3-dihydroxy-2-propoxymethyl)guanine A solution of 4.0 g of $N^2$-(4-methoxyphenyldiphenylmethyl)-9-(1,3-diacetoxy-2-propoxymethyl)guanine in 100 ml of methanol plus 20 ml of concentrated ammonium hydroxide was magnetically stirred at 22° C. for 16 hours then at 50° C. for 2.5 hours. An additional 10 ml of ammonium hydroxide were then added and the solution stirred another 2.5 hours at 50° C. Next, the solution was concentrated at reduced pressure and the residual solid recrystallized from methanol:ethyl acetate to give 3.5 g of $N^2$-(4-methoxyphenyldiphenylmethyl)-9-(1,3-dihydroxy-2-propoxymethyl)guanine, m.p. 148°–151° C.

Similarly proceeding as above in Part B the compounds prepared in Part A may be hydrolyzed to the following compounds:
2-(4-methoxyphenyldiphenylmethylamino)-6-methoxy-9-(1,3-dihydroxy-2-propoxymethyl)purine;
2-(4-methoxyphenyldiphenylmethylamino)-6-thio-9-(1,3-dihydroxy-2-propoxymethyl)purine;
2-(4-methoxyphenyldiphenylmethylamino)-6-methylthio-9-(1,3-dihydroxy-2-propoxymethyl)purine;
2,6-di-(4-methoxyphenyldiphenylmethylamino)-9-(1,3-dihydroxy-2-propoxymethyl)purine;
2-methylamino-6-di-(4-methoxyphenyldiphenylmethylamino)-9-(1,3-dihydroxy-2-propoxymethyl)purine;
2-(4-methoxyphenyldiphenylmethylamino)-9-(1,3-dihydroxy-2-propoxymethyl)purine;
6-chloro-2-(4-methoxyphenyldiphenylmethylamino)-9-(1,3-dihydroxy-2-propoxymethyl)purine;
2-(4-methoxyphenyldiphenylmethylamino)-9-(1,3-dihydroxy-2-propoxymethyl)purine; and
6-(4-methoxyphenyldiphenylmethylamino)-9-(1,3-dihydroxy-2-propoxymethyl)purine.

C.
$N^2$-(4-methoxyphenyldiphenylmethyl)-9-(1,3-din-octanoyloxy-2-propoxymethyl)guanine To a magnetically stirred solution of 1.05 g of $N^2$-(4-methoxyphenyldiphenylmethyl)-9-(1,3-dihydroxy-2-propoxymethyl)guanine and 25 mg of 4-dimethylaminopyridine in 30 ml of dry pyridine was added dropwise a solution of 1.2 g of n-octanoyl chloride in 10 ml of methylene chloride. After 15 hour, 1.5 ml of water was added and the solution concentrated at reduced pressure. The residue was chromatographed over silica gel eluting with 1:9 methanol:methylene chloride to give a white solid which was recrystallized from ethyl acetate:hexane to $N^2$-(4-methoxyphenyldiphenylmethyl)-9-(1,3-din-octanoyloxy-2-propoxymethyl)guanine.

Similarly, proceeding as in Part C above, the compounds from Part B may be esterified to the following compounds:
2-(4-methoxyphenyldiphenylmethylamino)-6-methoxy-9-(1,3-di-n-butanoyloxy-2-propoxymethyl)purine;
2-(4-methoxyphenyldiphenylmethylamino)-6-thio-9-[1,3-di-(2,2-dimethylpropanoyloxy)-2-propoxymethyl]purine;
2-(4-methoxyphenyldiphenylmethylamino)-6-thio-9-(1,3-di-n-octanoyloxy-2-propoxymethyl)-2-propoxymethyl)-purine;
2-(4-methoxyphenyldiphenylmethylamino)-6-thio-9-[1,3-di-(1-adamantylcarboxy)-2-propoxymethyl]purine;
2-(4-methoxyphenyldiphenylmethylamino)-6-methylthio-9-(1,3-di-n-heptanoyloxy-2-propoxymethyl)purine;
2,6-di-(4-methoxyphenyldiphenylmethylamino)-9-(1,3-di-n-decanoyloxy-2-propoxymethyl)purine;
2,6-di-(4-methoxyphenyldiphenylmethylamino)-9-(1,3-di-n-octanoyloxy-2-propoxymethyl)purine;
2,6-di-(4-methoxyphenyldiphenylmethylamino)-9-[1,3-di-(2,2-dimethylpropanoyloxy)-2-propoxymethyl]purine;
2,6-di-(4-methoxyphenyldiphenylmethylamino)-9-[1,3-di(1-adamantylcarboxy)-2-propoxymethyl]-purine;
2-methylamino-6-(4-methoxyphenyldiphenylmethylamino)-9-(1,3-di-n-tetradecanoyloxy-2-propoxymethyl)purine;
2-(4-methoxyphenyldiphenylmethylamino)-6-methylamino-9-(1,3-di-n-hexadecanoyloxy-2-propoxymethyl)purine;
6-chloro-2-(4-methoxyphenyldiphenylmethylamino)-9-(1,3-di-n-octadecanoyloxy-2-propoxymethyl)purine;
2-(4-methoxyphenyldiphenylmethylamino)-9-(1,3-di-n-octanoyloxy-2-propoxymethyl)purine;
2-(4-methoxyphenyldiphenylmethylamino)-9-[1,3-di-(2,2-dimethylpropanoyloxy)-2-propoxymethyl]purine;
2-(4-methoxyphenyldiphenylmethylamino)-9-[1,3-di-(1-adamantylcarboxy)-2-propoxymethyl]purine;
6-(4-methoxyphenyldiphenylmethylamino)-9-(1,3-di-n-dodecanoyloxy-2-propoxymethyl)purine;
$N^2$-(4-methoxyphenyldiphenylmethyl)-9-(1,3-dipropanoyloxy-2-propoxymethyl)guanine;
$N^2$-(4-methoxyphenyldiphenylmethyl)-9-(1,3-di-n-butanoyloxy-2-propoxymethyl)guanine;
$N^2$-(4-methoxyphenyldiphenylmethyl)-9-(1,3-di-(2-methylpropanoyloxy)-2-propoxymethyl)guanine;
$N^2$-(4-methoxyphenyldiphenylmethyl)-9-(1,3-di-n-pentanoyloxy-2-propoxymethyl)guanine;
$N^2$-(4-methoxyphenyldiphenylmethyl)-9-(1,3-di-(2,2-dimethylpropanoyloxy)-2-propoxymethyl)guanine;
$N^2$-(4-methoxyphenyldiphenylmethyl)-9-(1,3-di-n-hexanoyloxy-2-propoxymethyl)guanine;
$N^2$-(4-methoxyphenyldiphenylmethyl)-9-(1,3-di-n-heptanoyloxy-2-propoxymethyl)guanine;
$N^2$-(4-methoxyphenyldiphenylmethyl)-9-(1,3-di-n-decanoyloxy-2-propoxymethyl)guanine;
$N^2$-(4-methoxyphenyldiphenylmethyl)-9-(1,3-di-n-dodecanoyloxy-2-propoxymethyl)guanine;
$N^2$-(4-methoxyphenyldiphenylmethyl)-9-(1,3-di-n-tetradecanoyloxy-2-propoxymethyl)guanine;
$N^2$-(4-methoxyphenyldiphenylmethyl)-9-(1,3-di-n-hexadecanoyloxy-2-propoxymethyl)guanine clear oil;
$N^2$-(4-methoxyphenyldiphenylmethyl)-9-(1,3-di-n-octadecanoyloxy-2-propoxymethyl)guanine;
$N^2$-(4-methoxyphenyldiphenylmethyl)-9-(1,3-di-n-eicosanoyloxy-2-propoxymethyl)guanine; and
$N^2$-(4-methoxyphenyldiphenyl)-9-[1,3-di-(1-adamantylcarboxy)-2-propoxymethyl]guanine; m.p. 201°–203° C.;

N²-(4-methoxyphenyldiphenyl)-9-[1,3-di-(benzyloxy-acetyloxy)-2-propoxymethyl]guanine;

N²-(4-methoxyphenyldiphenyl)-9-[1,3-di-(3-benzyloxy-propanoyloxy)-2-propoxymethyl]guanine; and N²-(4-methoxyphenyldiphenyl)-9-[1,3-di-(4-benzyloxybutanoyloxy)-2-propoxymethyl]guanine.

D. 9-(1,3-Di-n-octanoyloxy-2-propoxymethyl)guanine

A solution of 0.969 g of N²-(4-methoxyphenyldiphenylmethyl)-9-(1,3-di-n-octanoyloxy-2-propoxymethyl)guanine in 40 ml of glacial acetic acid plus 10 ml of water was stirred at 75° C. for 3 hours. The solution was then concentrated and the residue chromatographed over silica gel eluting with 1:15 methanol:methylene chloride to give a white solid. The product was recrystallized from methanol to afford 0.385 g of 9-(1,3-di-n-octanoyloxy-2-propoxymethyl)guanine, m.p. 165°–166° C.

Similarly, proceeding as in Part D of the above example, using the compounds of Part C the following compounds may be prepared:

2-amino-6-methoxy-9-(1,3-di-n-butanoyloxy-2-propoxymethyl)purine;

2-amino-6-thio-9-[1,3-di-(2,2-dimethylpropanoyloxy)-2-propoxymethyl]purine;

2-amino-6-thio-9-[1,3-di-n-octanoyloxy-2-propoxymethyl]purine;

2-amino-6-thio-9-[1,3-di-(1-adamantylcarboxy)-2-propoxymethyl]purine;

2-amino-6-methylthio-9-(1,3-di-n-heptanoyloxy-2-propoxymethyl)purine;

2,6-di-amino-9-(1,3-di-n-decanoyloxy-2-propoxymethyl)purine;

2,6-di-amino-9-(1,3-di-n-octanoyloxy-2-propoxymethyl)purine;

2,6-diamino-9-[1,3-di-(2,2-dimethylpropanoyloxy)-2-propoxymethyl]purine;

2,6-di-amino-9-[1,3-di-(1-adamantylcarboxy)-2-propoxymethyl]purine;

2-methylamino-6-amino-9-(1,3-di-n-tetradecanoyloxy-2-propoxymethyl)purine;

2-amino-6-methylamino-9-(1,3-di-n-hexadecanoyloxy-2-propoxymethyl)purine;

2-chloro-6-amino-9-(1,3-di-n-octadecanoyloxy-2-propoxymethyl)purine;

2-amino-9-(1,3-di-octanoyloxy-2-propoxymethyl)purine;

2-amino-9-[1,3-di-(2,2-dimethylpropanoyloxy)-2-propoxymethyl]purine;

2-amino-9-[1,3-di-(1-adamantylcarboxy)-2-propoxymethyl]purine;

6-amino-9-(1,3-di-n-dodecanoyloxy-2-propoxymethyl)purine;

9-(1,3-dipropanoyloxy-2-propoxymethyl)guanine m.p. 191°–193° C.;

9-(1,3-di-n-butanoyloxy-2-propoxymethyl)guanine m.p. 199°–201° C.;

9-[1,3-di-(2-methylpropanoyloxy)-2-propoxymethyl]guanine;

9-(1,3-di-n-pentanoyloxy-2-propoxymethyl)guanine m.p. 193°–198° C.;

9-[1,3-di-(2,2-dimethylpropanoyloxy)-2-propoxymethyl]guanine m.p. 230°–232° C.;

9-(1,3-di-n-hexanoyloxy-2-propoxymethyl)guanine m.p. 179°–181° C.;

9-(1,3-di-n-heptanoyloxy-2-propoxymethyl)guanine;

9-(1,3-di-n-decanoyloxy-2-propoxymethyl)guanine m.p. 158°–160° C.;

9-(1,3-di-n-dodecanoyloxy-2-propoxymethyl)guanine m.p. 162°–164° C.;

9-(1,3-di-n-tetradecanoyloxy-2-propoxymethyl)guanine 137°–140° C.;

9-(1,3-di-n-hexadecanoyloxy-2-propoxymethyl)guanine m.p. 150°–154° C.;

9-(1,3-di-n-octadecanoyloxy-2-propoxymethyl)guanine;

9-(1,3-di-n-eicosanoyloxy-2-propoxymethyl)guanine;

9-[1,3-di-(1-adamantylcarboxy)-2-propoxymethyl]guanine m.p. 283°–285° C.;

9-[1,3-di-(2-butenoyloxy)-2-propoxymethyl]guanine;

9-[1,3-di-(4-octenoyloxy)-2-propoxymethyl]guanine;

9-[1,3-di-(9-dodecenoyloxy)-2-propoxymethyl]guanine;

9-[1,3-di-(cis-9-hexadecenoyloxy)-2-propoxymethyl]guanine;

9-[1,3-di-(cis-9-octadecenoyloxy)-2-propoxymethyl]guanine;

9-[1,3-di-(9,12-octadecadienoyloxy)-2-propoxymethyl]guanine; and

9-[1,3-di-(9,12,15-octadecatrienoyloxy)-2-propoxymethyl]guanine.

Similarly, catalytically removing the benzyl group and then proceeding as in Part D of the above example the following compounds, for example, are prepared:

9-[1,3-di-(hydroxyacetyloxy)-2-propoxymethyl]guanine;

9-[1,3-di-(3-hydroxypropanoyloxy)-2-propoxymethyl]guanine; and

9-[1,3-di-(4-hydroxybutanoyloxy)-2-propoxymethyl]guanine.

EXAMPLE 5

To 0.26 g of N²-acetyl-9-(1,3-dihydroxy-2-propoxymethyl)guanine from preparation V, Part B and 10 mg of 4-dimethylaminopyridine in a solution of 7 ml of pyridine was added 0.764 g of adamantanecarboxylic acid chloride as a solution in 3 ml of methylene chloride. The solution was magnetically stirred for 18 hours at 21° C. then 1 ml of water was added. After stirring an additional hour the solution was concentrated and the residue was treated for 16 hours with 10 ml of methanol containing 1 ml of concentrated ammonium hydroxide. The solution was concentrated and the residue was triturated with methanol to give 0.277 g of 9-[1,3-di(1-adamantylcarboxy)-2-propoxymethyl]guanine, m.p. 283°–285° C.

Similarly, proceeding as above using the appropriate acid chloride and the appropriate compound of formula (IX) or (XIV) wherein A is hydrogen the following compounds, for example, are prepared:

2-amino-6-methoxy-9-[1,3-di-(2,2-dimethylpropanoyloxy)-2-propoxymethyl]purine;

2-amino-6-thio-9-(1,3-di-n-octanoyloxy-2-propoxymethyl)purine;

2-amino-6-methylthio-9(1,3-di-n-decanoyloxy-2-propoxymethyl)purine;

2,6-diamino-9-(1,3-di-n-dodecanoyloxy-2-propoxymethyl)purine;

2-methylamino-6-amino-9-(1,3-di-n-tetradecanoyloxy-2-propoxymethyl)purine;

2-amino-6-methylamino-9-(1,3-di-n-hexadecanoyloxy-2-propoxymethyl)purine;

2-chloro-6-amino-9-(1,3-di-n-octadecanoyloxy-2-propoxymethyl)purine;

2-amino-9-[1,3-di-(1-adamantylcarboxy)-2-propoxymethyl]purine;

6-amino-9-[1,3-di-(4-octenoyloxy)-2-propoxymethyl]purine;

9-[1,3-di-(2,2-dimethylpropanoyloxy)-2-propoxymethyl]guanine;
9-(1,3-di-n-octanoyloxy-2-propoxymethyl)guanine;
9-(1,3-di-n-decanoyloxy-2-propoxymethyl)guanine;
9-(1,3-di-n-dodecanoyloxy-2-propoxymethyl)guanine;
9-(1,3-di-n-tetradecanoyloxy-2-propoxymethyl)guanine;
9-(1,3-di-n-hexadecanoyloxy-2-propoxymethyl)guanine;
9-(1,3-di-n-octadecanoyloxy-2-propoxymethyl)guanine;
9-(1,3-di-n-eicosanoyloxy-2-propoxymethyl)guanine;
9-[1,3-di-(4-octenoyloxy)-2-propoxymethyl]guanine;
9-[1,3-di-(9-dodecenoyloxy)-2-propoxymethyl]guanine;
9-[1,3-di-(cis-9-hexadecenoyloxy)-2-propoxymethyl]guanine;
9-[1,3-di-(cis-9-octadecenoyloxy)-2-propoxymethyl]guanine;
9-[1,3-di-(9,12-octadecadienoyloxy)-2-propoxymethyl]guanine;
9-[1,3-di-(9,12,15-octadecatrienoyloxy)-2-propoxymethyl]guanine; and
9-(1,3-dibenzoyloxy-2-propoxymethyl)guanine, m.p. 242°–243° C.

EXAMPLE 6

A.

$N^2$-(4-methoxyphenyldiphenylmethyl)-9-[1-hydroxy-3-(4-methoxyphenyldiphenylmethoxy)-2-propoxymethyl]guanine To 2 g of 9-(1,3-dihydroxy-2-propoxymethyl)guanine in N,N-dimethylformamide (50 ml) was added 6.33 g of 4-methoxyphenyldiphenylmethyl chloride, 20 mg of N,N-dimethylaminopyridine, and 10 ml of triethylamine. The reaction was stirred at 50°–60° C. for 60 hours then precipitated in ice water (900 ml). The precipitate was isolated by filtration and the product recrystallized from ethanol. The slightly impure product was further purified by column chromatography on silica gel eluting with 1:9 methanol:methylene chloride to yield 3.5 g $N^2$-(4-methoxyphenyldiphenylmethyl)-9-[1-hydroxy-3-(4-methoxy-phenyldiphenylmethoxy)-2-propoxymethyl]guanine after recrystallization from methanol, m.p. 159°–161° C.

Similarly, proceeding as in Part A above substituting the appropriate compounds of formula (XIV) wherein A is hydrogen for 9-(1,3-dihydroxy-2-propoxymethyl)-guanine and using the appropriate amount of 4-methoxyphenyldiphenylmethyl chloride the following compounds for example, are prepared:

2-(4-methoxyphenyldiphenylmethylamino)-6-methoxy-9-[1-hydroxy-3-(4-methoxyphenyldiphenylmethoxy)-2-propoxymethyl]purine;
2-(4-methoxyphenyldiphenylmethylamino)-6-thio-9-[1-hydroxy-3-(4-methoxyphenyldiphenylmethoxy)-2-propoxymethyl]purine;
2-(4-methoxyphenyldiphenylmethylamino)-6-methylthio-9-[1-hydroxy-3-(4-methoxyphenyldiphenylmethoxy)-2-propoxymethyl]purine;
2,6-di-(4-methoxyphenyldiphenylmethylamino)-9-[1-hyroxy-3-(4-methoxyphenyldiphenylmethoxy)-2-propoxymethyl]purine;
2-methylamino-6-(4-methoxyphenyldiphenylmethylamino)-9-[1-hydroxy-3-(4-methylphenyldiphenylmethoxy)-2-propoxymethyl]purine;
2-(4-methoxyphenyldiphenylmethylamino)-6-methylamino-9-[1-hydroxy-3-(4-methoxyphenyldiphenylmethoxy)-2-propoxymethyl]purine;
2-chloro-6-(4-methoxyphenyldiphenylmethylamino)-9[1-hydroxy-3-(4-methoxyphenyldiphenylmethoxy)-2-propoxy-methyl]purine;
2-(4-methoxyphenyldiphenylmethylamino)-9-[1-hydroxy-3-(4-methoxyphenyldiphenylmethoxy)-2-propoxymethyl]purine;
6-(4-methoxyphenyldiphenylmethylamino)-9-[1-hydroxy-3-(4-methoxyphenyldiphenylmethoxy)-2-propoxymethyl]purine;
2-methylamino-6-ethoxy-9-[1-hydroxy-3-(4-methoxyphenyldiphenylmethoxy)-2-propoxymethyl]purine;
2-n-butylamino-6-thio-9-[1-hydroxy-3-(4-methoxyphenyldiphenylmethoxy)-2-propoxymethyl]purine;
2-dimethylamino-6-methylthio-9-[1-hydroxy-3-(4-methoxyphenyldiphenylmethoxy)-2-propoxymethyl]purine;
2,6-diazido-9-[1-hydroxy-3-(4-methoxyphenyldiphenylmethoxy)-3-hydroxy-2-propoxymethyl]purine;
2,6-di(methylamino)-9-[1-hydroxy-3-(4-methoxyphenyldiphenylmethoxy)-2-propoxymethyl]purine;
2-chloro-6-methylamino-9-[1-hydroxy-3-(4-methoxyphenyldiphenylmethoxy)-2-propoxymethyl]purine;
2-azido-6-ethylamino-9-[1-hydroxy-3-(4-methoxyphenyldiphenylmethoxy)-2-propoxymethyl]purine;
2-dimethylamino-9-[1-hydroxy-3-(4-methoxyphenyldiphenylmethoxy)-2-propoxymethyl]purine;
6-methylamino-9-[1-hydroxy-3-(4-methoxyphenyldiphenylmethoxy)-2-propoxymethyl]purine;
6-dimethylamino-9-[1-hydroxy-3-(4-methoxyphenyldiphenylmethoxy)2-propoxymethyl]purine;
6-thio-9-[1-hydroxy-3-(4-methoxyphenyldiphenylmethoxy)-3-hydroxy-2-propoxymethyl]purine; and
6-methylthio-9-[1-hydroxy-3-(4-methoxyphenyldiphenylmethoxy)-3-hydroxy-2-propoxymethyl]purine.

B.

9-(1-n-Hexadecanoyloxy-3-hydroxy-2-propoxymethyl)guanine

To a stirred mixture of 3 g n-hexadecanoyl chloride in pyridine (50 ml) was added 1.5 g of $N^2$-(4-methoxyphenyldiphenylmethyl)-9-[hydroxy-3-(4-methoxyphenyldiphenylmethoxy-2-propoxymethyl]guanine. The reaction was stirred 48 hours at 50°–60° C. and then precipitated in ice water (500 ml). The resulting precipitate was treated with 80% acetic acid (aqueous) at 80° C. for one hour. The acetic acid was evaporated under reduced pressure and the residue chromatographed on a silica gel column eluting with 1:9 methanol:methylene chloride to yield 0.45 g 9-(1-n-hexadecanoyloxy-3-hydroxy-2-propoxymethyl)guanine after recrystallization from methanol m.p. 226°–227° C.

Similarly, proceeding as in Part B above substituting the appropriate acid chloride for n-hexadecanoyl chloride the following compounds, for example, are prepared:

2-amino-6-methoxy-9-(1-acetyloxy-3-hydroxy-2-propoxymethyl)purine;
2-amino-6-thio-9-[1-(2,2-dimethylpropanoyloxy)3-hydroxy-2-propoxy-methyl]purine;
2-amino-6-methylthio-9-[1-(2,2-dimethylpropanoyloxy)-3-hydroxy-2-propoxymethyl]purine;
2,6-diamino-9-[1-(2-methylpropanoyloxy)-3-hydroxy-2-propoxymethyl]purine;
2-methylamino-6-amino-9-(1-n-pentanoyloxy-3-hydroxy-2-propoxymethyl)purine;
2-amino-6-methylamino-9-(1-n-hexanoyloxy-3-hydroxy-2-propoxymethyl)purine;

2-chloro-6-amino-9-(1-n-heptanoyloxy-3-hydroxy-2-propoxymethyl)purine;
2-amino-9-(1-n-octanoyloxy-3-hydroxy-2-propoxymethyl)purine;
6-amino-9-(1-n-decanoyloxy-3-hydroxy-2-propoxymethyl)purine;
2-methylamino-9-(1-n-dodecanoyloxy-3-hydroxy-2-propoxymethyl)purine;
2-n-butylamino-6-thio-9-(1-n-tetradecanoyloxy-3-hydroxy-2-propoxymethyl)purine;
2-dimethylamino-6-methylamino-9-(1-n-hexadecanoyloxy-3-hydroxy-2-propoxymethyl)purine;
2,6-diazido-9-(1-octadecanoyloxy-3-hydroxy-2-propoxymethyl)purine;
2,6-di(methylamino)-9-(1-n-eicosanoyloxy-3-hydroxy-2-propoxymethyl)purine;
2-chloro-6-methylamino-9-(1-acetyloxy-3-hydroxy-2-propoxymethyl)purine;
2-azido-6-ethylamino-9-(1-propanoyloxy-3-hydroxy-2-propoxymethyl)purine;
2-dimethylamino-9-(1-n-butanoyloxy-3-hydroxy-2-propoxymethyl)purine;
6-methylamino-9-[1-(2-methylpropanoyloxy)-3-hydroxy-2-propoxymethyl]purine;
6-dimethylamino-9-(1-n-pentanoyloxy-3-hydroxy-2-propoxymethyl)purine;
6-thio-9-[1-(2,2-dimethylpropanoyloxy)-3-hydroxy-2-propoxymethyl]purine;
6-methylthio-9-(1-n-hexanoyloxy-3-hydroxy-2-propoxymethyl)purine;
9-(1-acetyloxy-3-hydroxy-2-propoxymethyl)guanine;
9-(1-n-butanoyloxy-3-hydroxy-2-propoxymethyl)guanine;
9-[1-(2,2-dimethylpropanoyloxy)-3-hydroxy-2-propoxymethyl]guanine;
9-[1-(2-methylpropanoyloxy)-3-hydroxy-2-propoxymethyl]guanine;
9-(1-n-pentanoyloxy)-3-hydroxy-2-propoxymethyl)guanine;
9-(1-n-hexanoyloxy)-3-hydroxy-2-propoxymethyl)guanine;
9-(1-n-heptanoyloxy)-3-hydroxy-2-propoxymethyl)guanine;
9-(1-n-octanoyloxy)-3-hydroxy-2-propoxymethyl)guanine m.p. 215.5°-217.5° C.;
9-(1-n-decanoyloxy)-3-hydroxy-2-propoxymethyl)guanine;
9-(1-n-dodecanoyloxy)-3-hydroxy-2-propoxymethyl)guanine;
9-(1-n-tetradecanoyloxy)-3-hydroxy-2-propoxymethyl)guanine;
9-(1-n-octadecanoyloxy)-3-hydroxy-2-propoxymethyl)guanine;
9-(1-n-eicosanoyloxy)-3-hydroxy-2-propoxymethyl)guanine;
9-(1-methoxyacetyloxy)-3-hydroxy-2-propoxymethyl)guanine;
9-[1-(1-adamantylcarboxy)-3-hydroxy-2-propoxymethyl]guanine;
9-(1-benzoyloxy-3-hydroxy-2-propoxymethyl)guanine;
9-[1-(2-butenoyloxy)-3-hydroxy-2-propoxymethyl]guanine;
9-[1-(4-octenoyloxy)-3-hydroxy-2-propoxymethyl]guanine;
9-[1-(9-dodecenoyloxy)-3-hydroxy-2-propoxymethyl]guanine;
9-[1-(cis-9-hexadecenoyloxy)-3-hydroxy-2-propoxymethyl]guanine;
9-[1-(9,12-octadecadienoyloxy)-3-hydroxy-2-propoxymethyl]guanine;
9-[1-(9,12,15-octadecatrionoyloxy)-3-hydroxy-2-propoxymethyl]guanine;
9-[1-(2-butenoyloxy)-3-hydroxy-2-propoxymethyl]guanine; and
9-[1-(3-carboxypropanoyloxy)-3-hydroxy-2-propoxymethyl]guanine m.p. 191°-192° C.

Similarly, catalytically removing the benzyl group and then proceeding as above the following compounds, for example, are prepared:
9-(1-hydroxyacetyloxy-3-hydroxy-2-propoxymethyl]guanine;
9-[1-(3-hydroxypropanoyloxy)-3-hydroxy-2-propoxymethyl]guanine; and
9-[1-(4-hydroxybutanoyloxy)-3-hydroxy-2-propoxymethyl]guanine.

EXAMPLE 7

A twofold stoichiometric excess of 3% hydrogen chloride in methanol is added to a solution of 1.0 g. of 9-(1,3-di-n-octanoyloxy-2-propoxymethyl)guanine in 20 ml methanol. Diethyl ether is added until precipitation is complete. The product is filtered, washed with ether, air dried and recrystallized to give 9-(1,3-di-n-octanoyloxy-2-propoxymethyl)guanine hydrochloride.

In a similar manner, all compounds of Formula I in free base form may be converted to the acid addition salts by treatment with the appropriate acid, for example, hydrochloric acid, hydrobromic acid, sulfuric acid, phosphoric acid, acetic acid, propionic acid, glycolic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, and the like.

EXAMPLE 8

1.0 g of 9-(1,3-di-n-octanoyloxy-2 propoxymethyl)-guanine HCl suspended in 50 ml of ether is stirred with a twofold stoichiometric excess of dilute aqueous potassium carbonate solution until the salt is completely dissolved. The organic layer is then separated, washed twice with water, dried over maganesium sulfate and evaporated to yield 9-(1,3-di-n-octanoyloxy-2-propoxy methyl)guanine as the free base.

Alkali metal salts of mono and diesters of formula I, particularly where $R^7$ is 1-adamantyl or 2-methyl-2-propyl may be prepared according to the following example.

EXAMPLE 9

The following example illustrates the preparation of representative pharmaceutical formulations containing an active compound of Formula (I) such as 9-[1,3-di-(2,2-dimethylpropanoyloxy-2-propoxymethyl]guanine.

| A. Topical Formulation | |
|---|---|
| Active compound | 0.2-2 g |
| Span 60 | 2 g |
| Tween 60 | 2 g |
| Mineral oil | 5 g |
| Petrolatum | 10 g |
| Methyl paraben | 0.15 g |
| Propyl paraben | 0.05 g |
| BHA (butylated hydroxy anisole) | 0.01 g |
| Water qs | 100 ml |

All of the above ingredients, except water, are combined and heated at 60° C. with stirring. A sufficient quantity of water at 60° C. is then added with vigorous stirring to provide 100 g of the cream formulation which is then cooled to room temperature.

The following formulation is useful for intraperitoneal and intramuscular injection.

| B. IP and IM Formulation | |
|---|---|
| Active compound | 0.5 g |
| Propylene glycol | 20 g |
| Polyethylene glycol | 20 g |
| Tween 80 | 1 g |
| 0.9% Saline solution qs | 100 ml |

The active compound is dissolved in propylene glycol, polyethylene glycol 400 and Tween 80. A sufficient quantity of 0.9% saline solution is then added with stirring to provide 100 ml of the I.P or I.M solution which is filtered through a 0.2 micron membrane filter and packaged under sterile conditions.

The following formulation is useful for intravenous injection.

| C. I.V. Formulation | |
|---|---|
| Active compound | 0.1 g |
| Polysorbate 80 | 0.1 g |
| Propylene glycal or polyethylene glycol 400 | 3.0 g |
| Water qs | 100 ml |

The active compound is added to a solution of polysorbate 80 and propylene glycol or polyethylene glycol 400 in 20 ml of water and mixed. The resulting solution is diluted with water to 100 ml and filtered through the appropriate 0.2 micron membrane filter.

| D. Tablet Formulation | |
|---|---|
| | Parts by weight |
| Active compound | 200 |
| Magnesium stearate | 3 |
| Starch | 30 |
| Lactose | 116 |
| PVP (polyvinylpyrrolidone) | 3 |

The above ingredients are combined and granulated using methanol as the solvent. The formulation is then dried and formed into tablets (containing 200 mg of active compound) with an appropriate tabletting machine.

EXAMPLE 10

The exceptional antiviral activity of the compound of the invention is illustrated by the following assay procedures:

The Herpes simplex virus 2 strain G for infection is prepared in HEp-2 cell cultures. Virus is adsorbed for 1 hour, fresh media is placed on the cells, and they are incubated at 35° C. until all cells were infected. The cell suspension is frozen at −70° C., thawed, and centrifuged to remove cell debris. The supernatant fluid is aliquoted and stored frozen at −70° C. until use. A 106.7 dilution of the supernatant fluid producer a 50% cell culture infective dose ($CCID_{50}$) in HEp-2 cells and a 103.7 dilution producer a 50% lethal challenge ($LC_{50}$) in mice.

Groups of 20 Swiss Webster female mice (15–17 gm), are challenged by intraperitoneal route using 0.2 ml of EMEM containing 10 $LC_{50}$/mouse of virus. Mice challenged with 100.5 more or less virus than the 10 $LD_{50}$ challenge serves as a virulence control to assure the model is working properly.

Treatment with test compounds begins 6 hours postchallenge. The mice, divided into groups of 20, are administered the compounds in saline s.c. at 5 mg/kg, 10 mg/kg and 20 mg/kg. One group of 20 mice is used as a control group and administered saline s.c. The treatment is repeated at 24, 48, 72 and 96 hours postchallenge.

Compounds of the instant invention show antiviral activity in the above test.

What is claimed is:

1. A compound of the formula $$\begin{array}{c} R^5 \quad R^6 \\ R^4-N \diagdown \diagup N \\ R^3 \diagdown N \diagup N \\ | \\ CH_2OCHCH_2OR^1 \\ | \\ CH_2OR^2 \end{array} \quad (I)$$

or a pharmaceutically acceptable acid addition salt thereof wherein
  $R^1$ and $R^2$ are both $-C(O)R^7$ wherein $R^7$ is 1-adamantyl;
  $R^3$ is amino;
  (a) $R^6$ is hydrogen or amino and $R^4$ together with $R^5$ is a bond; or
  (b) $R^5$ together with $R^6$ is a keto group and $R^4$ is hydrogen.

2. The compound of claim 1 wherein $R^5$ together with $R^6$ is a keto group and $R^4$ is hydrogen which is 9-[1,3-di-(1-adamantylcarboxy)-2-propoxymethyl]guanine.

3. A pharmaceutical composition which comprises a pharmaceutically acceptable carrier and a compound of claim 1.

4. A method of treating viral infection in a warm blooded or a cold blooded animal having a viral infection which comprises administering an effective amount of a compound of claim 1.

5. The pharaceutical composition of claim 3 wherein the pharmaceutically acceptable carrier is a liposome.

* * * * *